United States Patent [19]

Kleesattel

[11] 4,275,966

[45] Jun. 30, 1981

[54] METHOD AND APPARATUS FOR THE MEASUREMENT OF HARDNESS TESTING INDENTATIONS

[76] Inventor: Claus Kleesattel, Apartado 4969, San Jose, Costa Rica

[21] Appl. No.: 4,325

[22] Filed: Jan. 18, 1979

[51] Int. Cl.³ .................. G01B 11/22; G02B 27/17; G01N 3/40
[52] U.S. Cl. .................. 356/378; 73/81; 250/239; 350/6.2; 356/387
[58] Field of Search ........ 356/376, 375, 378, 371–379, 356/380, 32, 240, 445–478, 387; 73/78, 81, 85, 800

[56] References Cited

U.S. PATENT DOCUMENTS

| | | | |
|---|---|---|---|
| 2,216,943 | 10/1940 | Hanemann | 73/85 |
| 2,311,101 | 2/1943 | Tuttle et al. | 356/446 |
| 2,491,667 | 12/1949 | Kent | 73/81 |
| 3,776,995 | 12/1973 | Little, Jr. | 350/6.2 |
| 3,822,946 | 7/1974 | Rynkowski | 73/81 |
| 4,078,858 | 3/1978 | Mast | 356/446 |
| 4,112,309 | 9/1978 | Nakazawa et al. | 356/371 |
| 4,147,052 | 4/1979 | Tsujiuchi et al. | 73/81 |

FOREIGN PATENT DOCUMENTS 2331124  5/1975  Fed. Rep. of Germany ............. 73/81

*Primary Examiner*—John K. Corbin
*Assistant Examiner*—William H. Punter
*Attorney, Agent, or Firm*—Parmelee, Johnson, Bollinger & Bramblett

[57] ABSTRACT

Methods and apparatus are provided for determining the magnitude of hardness testing indentations by scanning the indentations with a light source with or without an external load being applied while the scanning takes place. The intensity of the reflected light from the surface under test is measured utilizing a light-senstive surface surrounding the measuring field. One or more diameters or the entire indentation is scanned and measured to determine the magnitude of the indentations.

5 Claims, 10 Drawing Figures

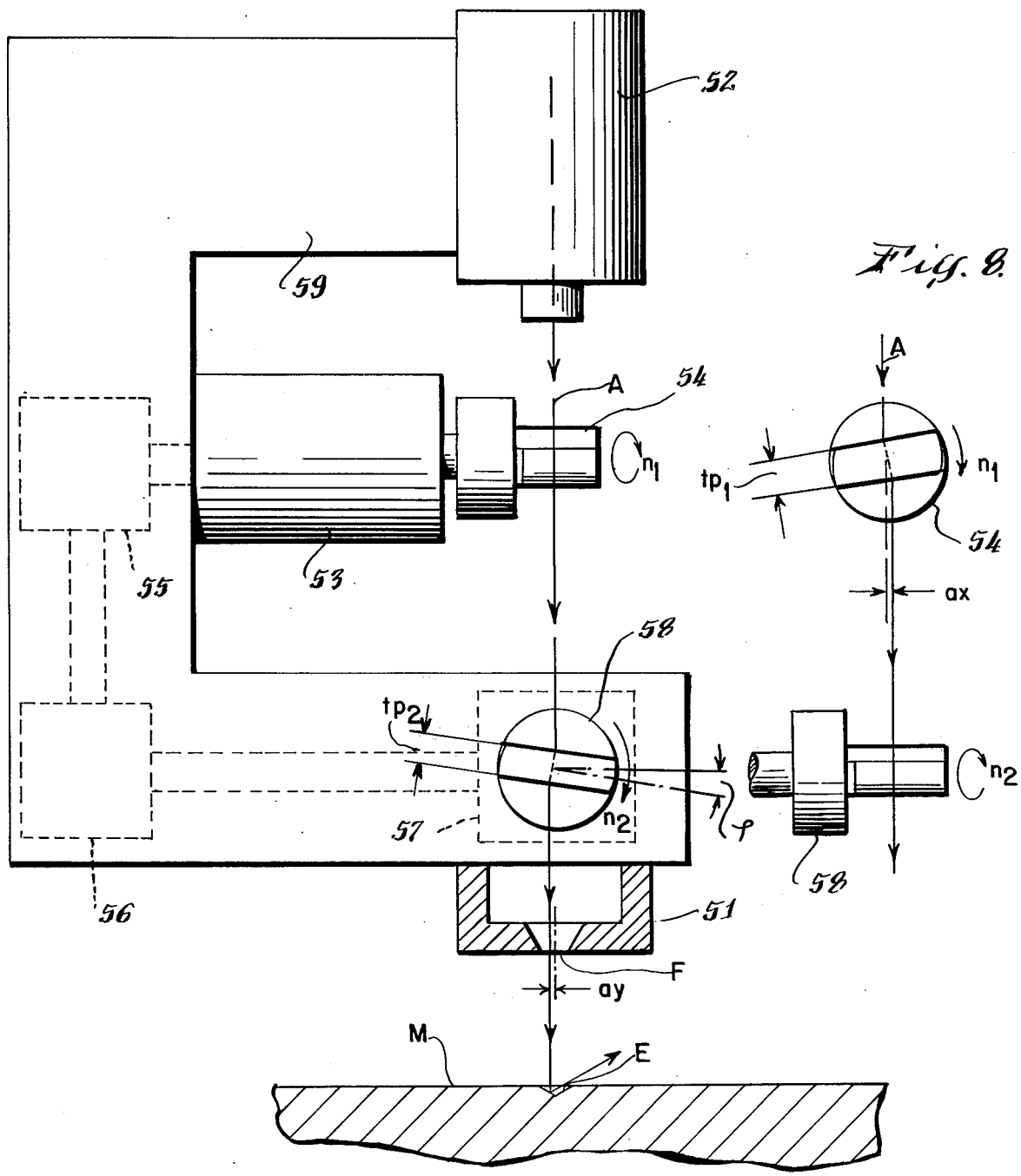

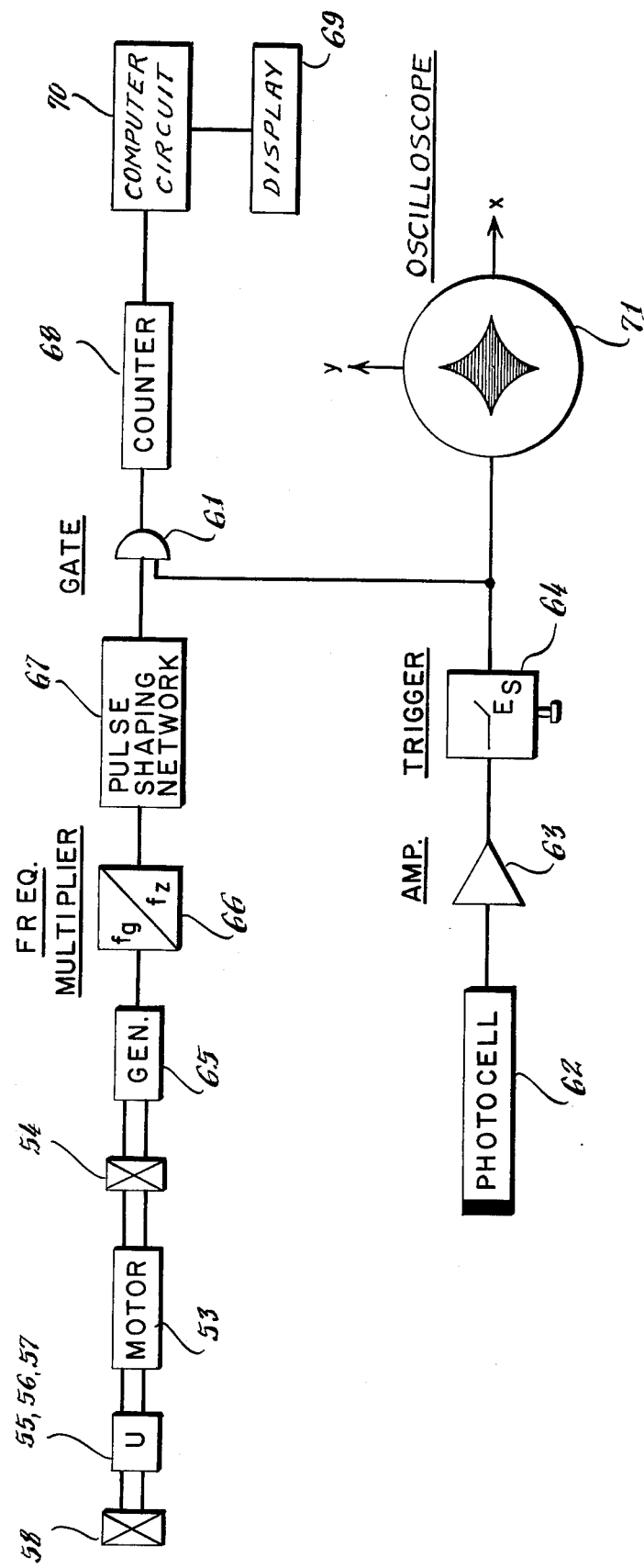

4,275,966

METHOD AND APPARATUS FOR THE MEASUREMENT OF HARDNESS TESTING INDENTATIONS

BACKGROUND OF THE INVENTION

The invention relates to methods and apparatus for measuring the magnitude of indentations made for testing the hardness of the surfaces of solid materials, and more particularly to such methods and apparatus which scan the indentations with a light source and measure the reflections thereon.

It is known in principle how to determine the magnitude of indentations, made by hardness testing equipment, with the help of opto-electronic devices. For instance, according to the German Patent disclosure OS No. 23 31 124, the solid surface containing an indentation is illuminated by a light beam in a specified direction. The portion of the light beam that is incident on the indented area is reflected in directions which differ from the direction of the reflected light coming from the undisturbed surface. This effect is utilized for generating an optical image of the indent and its surrounding region. This image is then quantitatively evaluated by a scanning technique which counts the number of picture elements in the image so generated.

One disadvantage the known scanning methods have is that they must rely on an enlarged image of the indentation. Consequently, the quantitative result of the measurement depends on the magnification factor of the magnifying system which has to be known and maintained constant. Furthermore, working with enlarged images of the indentation involves relatively large scanning fields which may create linearity problems. The lens aberrations must be considered as another source of possible measuring errors since the geometry of the image is not necessarily identical with the geometry of the indent.

SUMMARY OF THE INVENTION

Accordingly, it is an object of the present invention to provide a new and novel method and apparatus for the quantitative evaluation of indentations produced by hardness testing equipment by making direct measurements on the indentations without the use of image-forming optics thereby obviating the variable optical parameters associated therewith.

A further object of this invention is to provide a new and novel method and apparatus for measuring hardness testing indentations which is simple, easily applied and more accurate than prior techniques.

A further object of this invention is to provide a method and apparatus for measuring hardness testing indentations while the full testing load is being applied.

In attaining these and other objects and advantages and in carrying out this invention in the illustrative embodiments thereof, methods and apparatus are provided for scanning indentations in solid materials with a light source to determine the hardness of such materials with or without an external load being applied thereto. The intensity of the light reflected from the surface under test is measured utilizing a light-sensitive surface preferably formed as a surface of revolution about the optical axis of the light source. One or more diameters are scanned and measured or the entire indentation is scanned and measured with means being provided for determining the magnitude of the indentations in either scanning mode.

BRIEF DESCRIPTION OF THE DRAWINGS

The invention, both as to organization and method of operation, together with further objects and advantages thereof, may best be understood by reference to the following description taken in connection with the accompanying drawings, in which:

FIG. 7 is a schematic illustration showing one form of a scanning system of the present invention particularly suitable for making area measurements on indentations as made in hardness testing.

FIG. 8 is a partial side elevational view of the scanning system shown in FIG. 7.

FIG. 9 is a schematic block diagram illustrating one form of a complete system for the present invention.

DESCRIPTION OF THE PREFERRED EMBODIMENTS

Figure 1:
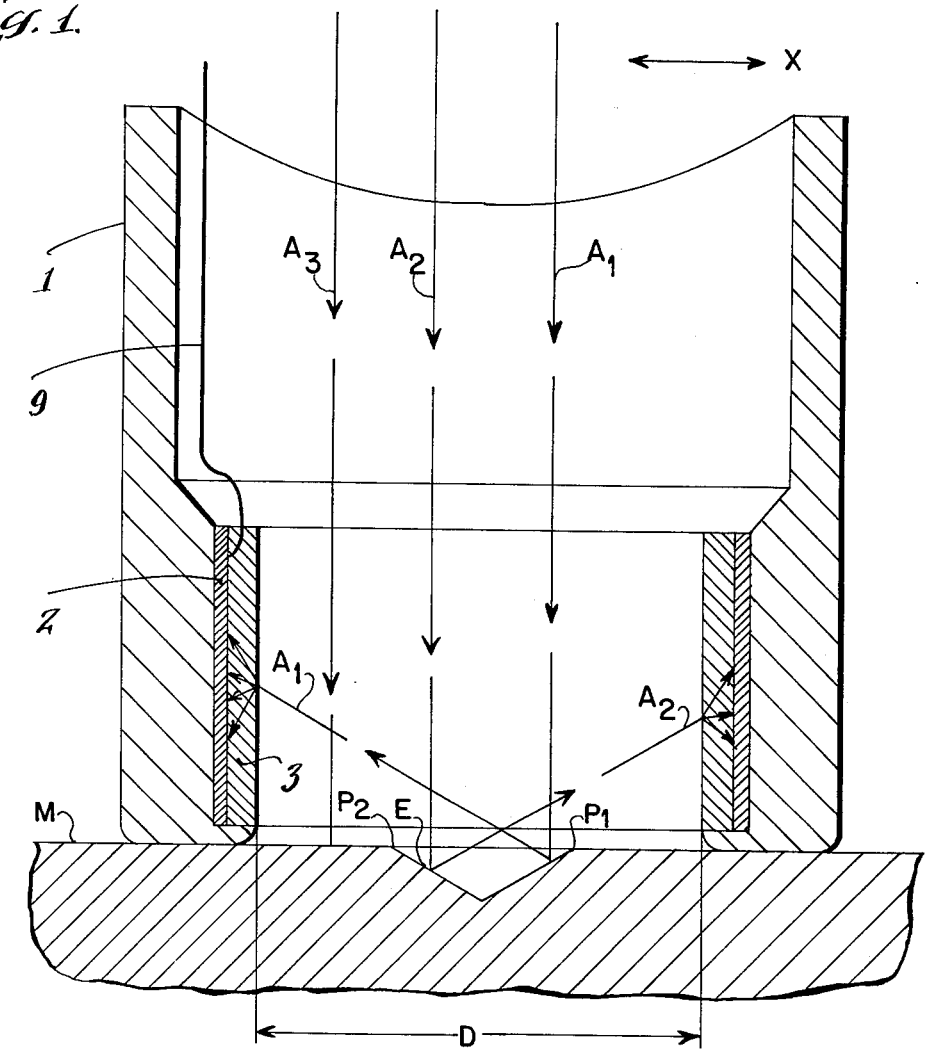
FIG. 1 is an axial sectional view of one embodiment showing the portion of the measuring system of this invention which is put on the surface of a testpiece.

Before providing a more detailed description of the invention in connection with the illustrative embodiments in the drawings, a general discussion of various aspects of the invention will first be presented.

The diameter of the light beam, which is directed against the surface to be tested, is chosen in accordance with the area of the indentation to be measured. In order to obtain an adequate measuring accuracy, the ratio of light spot area to indentation area must be properly selected. Generally, an area ratio on the order of magnitude of 1:100 or less is considered to be adequate. For rather small indentation areas, e.g. from 0.01 to 0.1 $mm^2$, the use of a light source producing monochromatic, coherent light is indicated, e.g. a laser with a beam expander and a focussing lens. Employing the latter, it is possible to obtain focal spots of less than 50 $\mu m$ diameter at a relatively large focal distance and with a beam convergence angle of 2 degrees, or so. If such a light source is used, the distance between the focussing lens and the testpiece surface is not critical. In such case, the usual means for the focus control is not required.

Normal, incoherent light will suffice for producing a sufficiently small light spot if larger indents, e.g. from 1 to 30 mm$^2$ area, are to be measured.

For determining the intensity of the reflected light, a suitable light-sensitive surface is employed, for instance a photocell, a photoresistor, or an ordinary selenium cell. These cells are dimensioned and positioned in such a way that they receive mainly either the light which is reflected from the indent, or the light which is reflected from the area (of predetermined size) surrounding the indent. The light-sensitive surface is concentric and preferably formed as a surface of revolution about the optical axis of the device. Care has to be taken to minimize the incidence of scattered light on the light-sensitive surface coming from other directions.

There are two basic modes of operation for practicing the new measuring technique in accordance with this invention. In the first mode, one or more diameters of the indentation are measured from which the hardness is determined. This mode of operation is applicable mainly to cone and ball indentations of relatively large size. If the material is anisotropic, the measurement of two orthogonal diameters is recommended.

The displacement of the light spot can be accomplished, for example, by moving the light source, which is linked mechanically with a micrometer, in a lateral direction. If use is made of such a simple setup, then it is particularly advantageous to direct the light beam through the indenter towards the surface being tested, since the light beam can then be centered in such a way that it must run through the center point of the indenter when the light source is displaced laterally. This approach eliminates a requirement for additional optical means for proper alignment.

Figure 10:
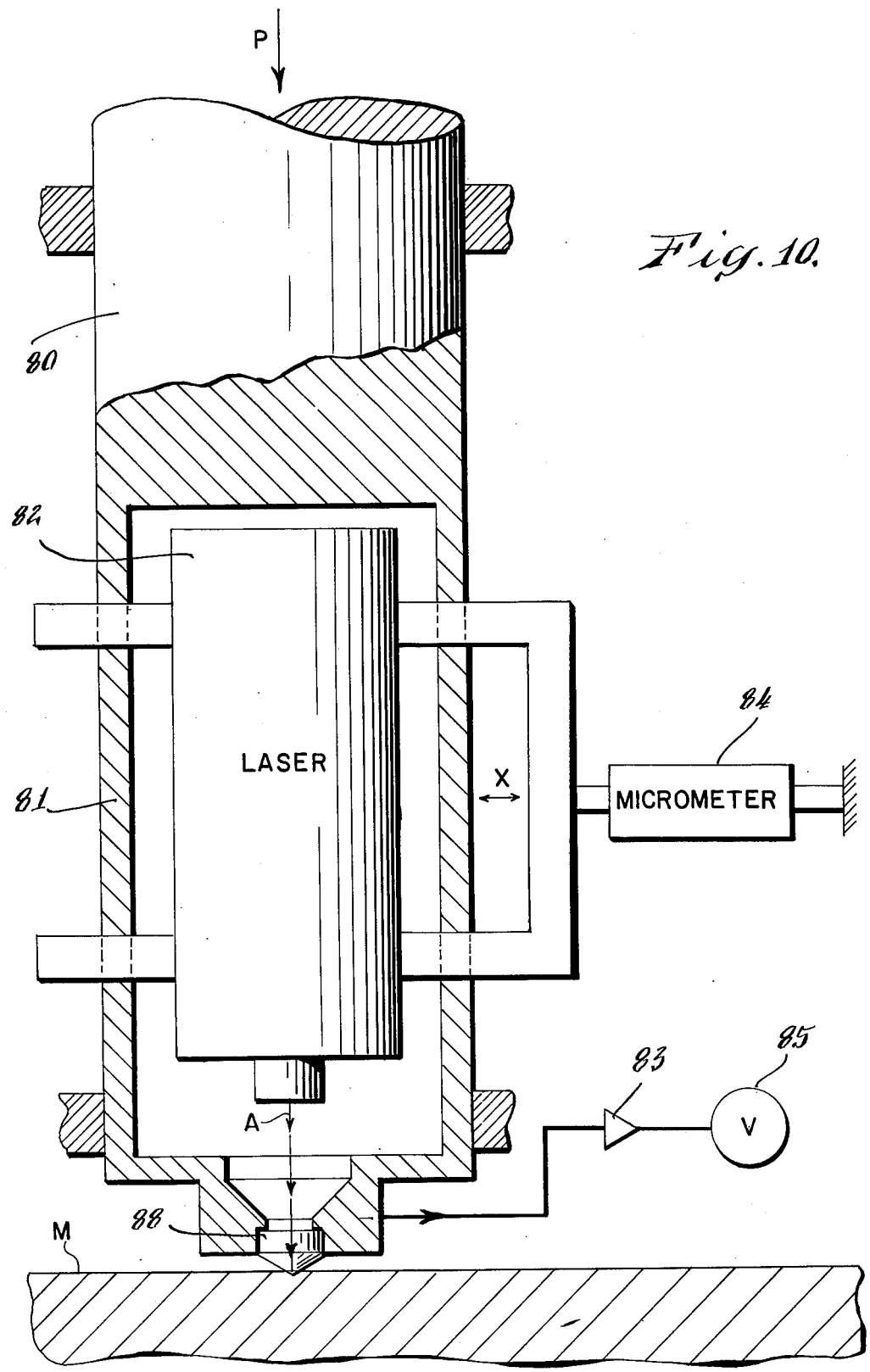
FIG. 10 is a partial, axial semi-schematic sectional view of an embodiment applicable to the measurement of indentation diameters.

Furthermore, it is preferred for this type of setup to have a rectilinear trajectory for the light spot. If the light intensity of the light reflected from the indent itself is measured, an intensity increase takes place during the crossing of the first edge of the indent, and an intensity decrease occurs when the second edge is crossed. A more detailed description of this arrangement which is illustrated in FIG. 10 will be given hereinafter.

With respect to the second mode of operation of the measuring system of the present invention, it is emphasized that the well-known, fundamental definition of indentation hardness is based upon the real indentation area. Now, in the case of Vickers indentations the difference between the area calculated from the diagonal lengths on one hand and the real area on the other hand may amount to as much as 25 percent, for example, when the shape of the indent is strongly astroidic (pin cushion geometry).

Accordingly, the measuring system of this invention may be used for determining the area of the indentation by scanning the entire indentation so that its true area can be directly evaluated. The light beam is repeatedly scanned rectilinearly in the X-direction at a constant velocity and periodically displaced in the Y-direction such that a scanning raster is traced over the entire area of the indentation. The area measurement is reduced to a time measurement between indentation edges for each scan line by the counting of electrical pulses generated therebetween, a procedure which can be carried out automatically. This will be described in more detail hereinafter in connection with the preferred embodiments.

In accordance with this invention, both the distance and area measurements can be made on indentations from which the indenter has been removed and through the indenter while the test load is being applied, i.e. under load.

It will become evident from the following description of the embodiments that the practical implementation of the present method does not require calibration. The numerical result of the measurements is independent of variable parameters like optical magnification, amplification factors or such electronic quantities as resistance, capacitance and the like.

As a first step, the principle of determining the area or the diameter of hardness test indentations will be explained with reference to FIGS. 1 and 2.

Figure 2:
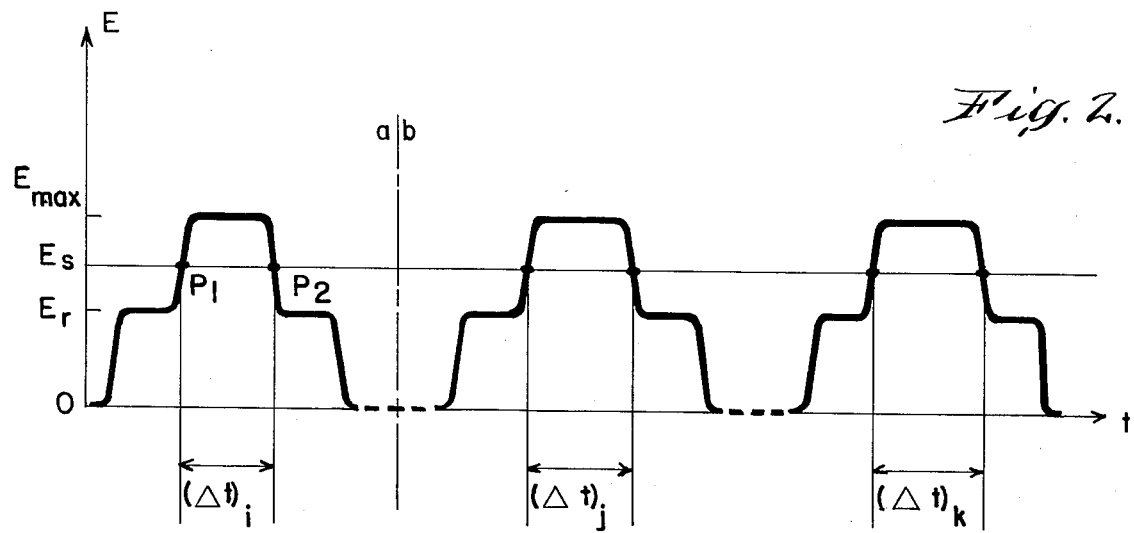
FIG. 2 is a diagram illustrating the type of voltage as a function of time or lateral displacement generated by the detection of reflected light from indentations being measured in accordance with this invention.

FIG. 1 shows a simple embodiment consisting of a tubular part 1 which is put on the testpiece surface M such that the indentation E lies at or near the axis of the tubular part 1. Light in the form of a sharp, slightly convergent beam, e.g. the focussed beam of a laser, is directed against the testpiece surface M as indicated by the three single rays $A_1$, $A_2$ and $A_3$, i.e. for three different positions of the light beam. The light beam passes through a scanner (not shown) before it reaches the lower portion of part 1. The scanner deflects the beam in two directions namely in the X-direction, as indicated by the arrow, and in the Y-direction, i.e. in a direction which is perpendicular both to the X-direction and the drawing plane. The light ray meets the testpiece surface M at normal incidence (90°), and its lateral displacement is realized in such a way that it will not change its direction so that measuring errors due to angular deviations are avoided. The surface of the indentation E is supposed to be almost mirror-like so that the light rays A undergo virtually specular reflection therefrom. This condition is well fulfilled for most metals. Light rays which fall within indentations of conical or pyramidal shape, as $A_1$ and $A_2$, are reflected in a lateral direction and are applied to a light-sensitive surface or layer 2 which is located at the inner wall of tubular part 1, near its open end. The light-sensitive surface 2 can be part of a photocell, a photoresistor, or a photovoltaic cell, e.g. selenium cell. (The light-sensitive surface is preferably formed as a surface of revolution about the axis of the tubular element). A diffuser 3 may be added to the light-sensitive layer 2 in order to obtain a wider distribution of the reflected light beam on the light-sensitive surface 2. The light-sensitive surface 2 of the device, i.e. its photodetector is connected to circuits and evaluation units which are not shown in FIG. 1.

Those rays which strike the testpiece surface M outside the indented area E, like ray $A_3$, are predominantly reflected without any change of direction provided that the material's surface is sufficiently smooth. They are propagated upwards into the bore of part 1 without reaching the light-sensitive layer 2.

The deflection of the light beam takes place in such a manner that the light spot striking the testpiece surface M runs at a constant velocity over a field of diameter D in the X-direction. Depending on the intensity of the reflected light, the light-sensitive layer 2 (usually in conjunction with other electronic components) generates a voltage E(t) as shown in the left portion (a) of the diagram presented in FIG. 2. The curve would have the same shape if the beam displacement X is substituted for the time t on the abscissa.

The points $P_1$ and $P_2$ correspond to the two edges of the indent E. The transverse dimension of the indentation can be calculated from the measured time difference $\Delta t$ (See FIG. 2) if the deflection velocity $V_x$ of the light beam is both constant and known. If the light beam, after each crossing in the X-direction, is deflected by one line width in the Y-direction, then a sequence of voltage pulses with varying pulse width $\Delta t$ are generated, as illustrated in FIG. 2. If the entire indentation area is scanned in this manner, the indentation area follows from the expression below.

$$A = b_y V_x \Sigma(\Delta t) \qquad (1)$$

where $b_y$ is the line-width of the scanning operation. Details for the scanning mechanism of the light beam and to the electronic evaluation of the voltage pulses are provided hereinafter.

Figure 3:
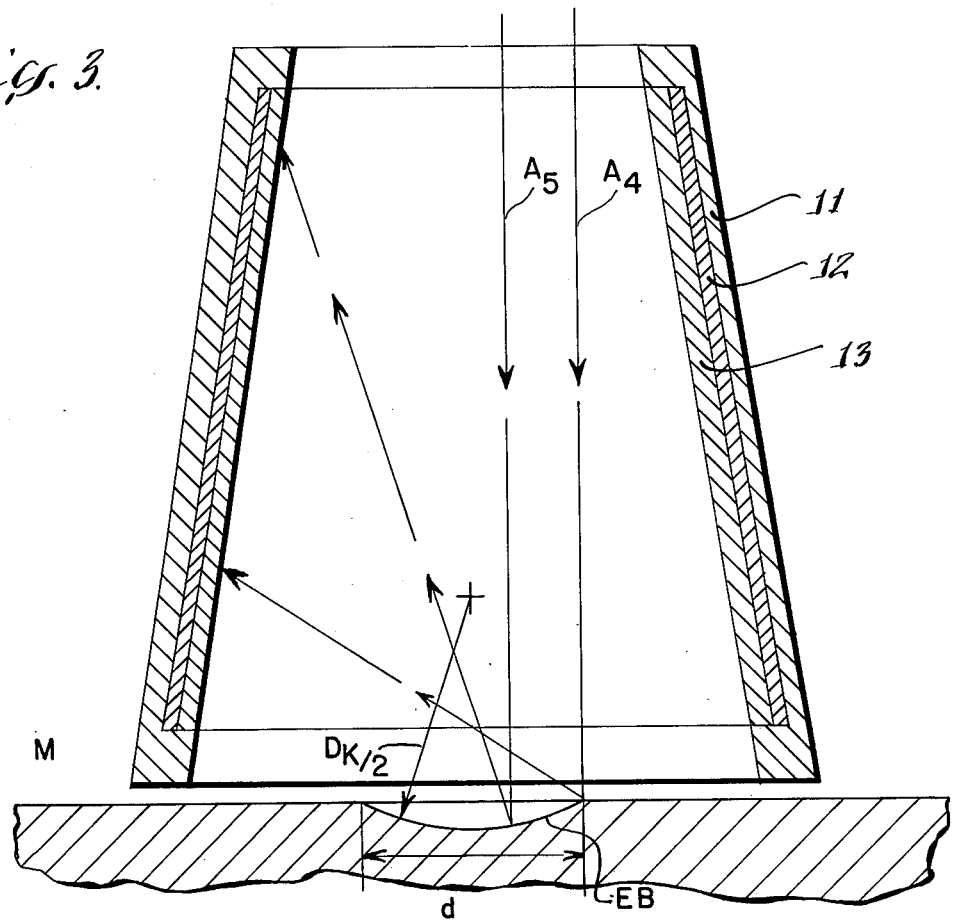
FIG. 3 is an axial sectional view of another embodiment showing the portion analogous to FIG. 1 for measuring another type of indentation.

The method outlined above is, in principle, not only applicable to measurements on conical or pyramidal indents, but also to spherical ones, as produced in Brinell testing machines. An embodiment adapted to the evaluation of spherical indents (ball indentations) is shown in FIG. 3, which again contains only part of the device. A slightly conical, tubular part 11 is placed on the testpiece surface M so that the indent EB lies at or near the center line or axis of part 11 while a light beam, which may be scanned in the X- and Y-directions, is introduced from above.

Light rays $A_4$ and $A_5$ indicate two positions of the central ray of the incident light beam which is scanned across spherical indent EB. The light rays reflected from the indented region spread over a relative big angular range owing to the spherical geometry of the indent EB. The limits of the angular range follow from the standards for Brinell hardness testing in accordance with which the indentation must not be smaller than 0.25 $D_k$, and not bigger than 0.6 $D_k$, where $D_k$ is the diameter of the ball indenter. The light-sensitive layer 12 with its diffuser 13 has to be shaped accordingly and is preferably formed as a surface of revolution about the optical axis of part 11. Light being directly reflected from the center portion of the indent EB does not reach the light-sensitive surface 12. Therefore, a "hole" will appear in the voltage curve which, however, can be masked in the electronic evaluation system by applying methods which are well-known to those skilled in the art. Otherwise, the measuring procedure for ball or spherical indents is analogous to the one outlined before for conical and pyramidal indentations.

The embodiments described so far are quite simple and should be adequate for many hardness testing jobs. It is to be noted, however, that common technical surfaces generally do not have the properties of an ideal reflector. Usually, the incident light is reflected in more than one direction, i.e. scattering takes place due to the surface roughness or due to marks left on the surface from machining and finishing processes which have been applied to the workpiece. The light scattered from a dull or rough surface diminishes the "contrast", i.e. the voltage ratio $E_{max}/E_r$ as shown in FIG. 2. To avoid this loss of contrast, means can be incorporated into the device for making the voltage ratio as big as possible under such conditions.

Figure 4:
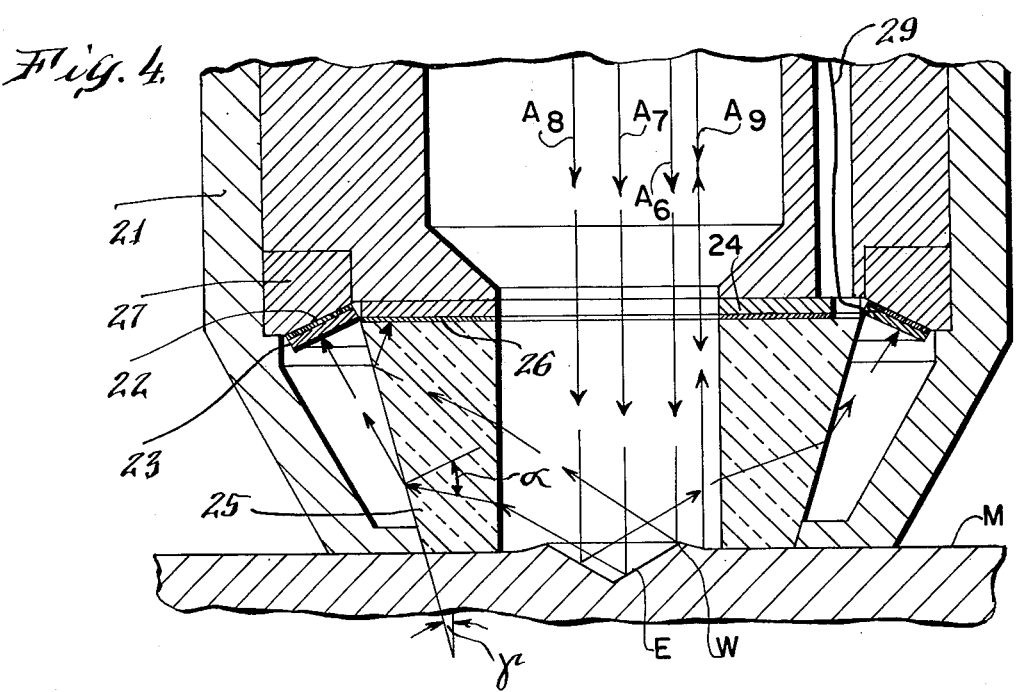
FIG. 4 is an axial sectional view of another embodiment of parts analogous to FIG. 1.

In addition to the light that is scattered from the surface of the testpiece outside the indent still other undesired light rays may reach the photocell. In this context, it should be mentioned that the edges of indentations are not always sharp. Quite often such edges possess a certain roundness caused by the piling-up of material displaced during the indentation process, such as illustrated in FIG. 4 by an area marked 'W'. The indent E produced in the material surface M possesses a slight bulge at its periphery (area W), shown in exaggerated form in FIG. 4. A light ray $A_6$ incident upon this bulging region W is reflected in a direction that differs from the reflection angle of the rays being reflected by the indentation itself. Compare $A_6$ with $A_7$, for example. Because of this, it is advantageous to provide the light-sensitive layer with means that make it directional so that it can be reached only by light rays which are incident within a specified range of angles. Rays arriving at other angles are rejected, i.e. they are deflected in other directions, or absorbed, or simply reflected, depending on the kind of angle limiting device being applied.

Means for limiting the angle of incidence are contained in the device shown in FIG. 4. The illustration depicts again a tubular part 21, put on the surface M which has been indented, having the deflectable light beam entering through the upper portion thereof. Different positions of the light beam are indicated by the rays $A_6$ through $A_9$.

In the lower portion of part 21, right below an inset part 24, a vitrious body 25 is placed, having a cylindrical bore in its center and having an external surface which is conically shaped, where the cone angle $\gamma$ is of such magnitude that the angle of incidence $\alpha$ of the light rays reflected from the indent E, rays $A_7, A_8$, comes close to the critical angle $$\alpha_{crit} = \arcsin(1/n_{gk}) \qquad (2)$$

where $n_{gk}$ is the index of refraction of the transparent body 25. The rays $A_7$, $A_8$ do reach a diffuser layer 23 and subsequently the light-sensitive layer 22. The latter, as before, is connected through wire leads to the electronic evaluation system. Rays marked $A_6$ reflected from the rounded edge W of the indent E arrive at steeper angles $\alpha > \alpha_{crit}$ at the outer surface of the glass body 25 and experience total reflection there, striking finally a light-absorbing layer 26 which is attached to the upper face of the transparent body 25.

In principle it is possible to utilize the free space between the glass body 25 and part 21 for setting up a pattern of multiple reflections so that the incident ray travels back and forth in the free space thereby providing more uniform light distribution reaching the light-sensitive layer 22.

Figure 5:
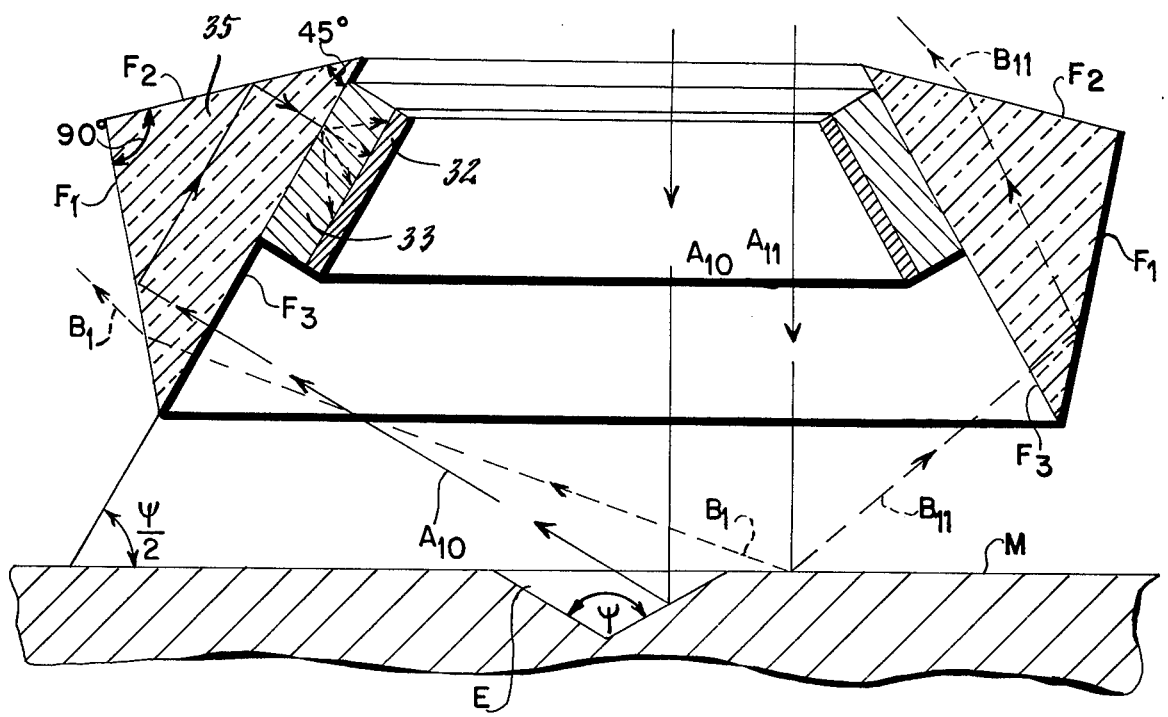
FIG. 5 is an axial sectional view showing a portion of the measuring device of the present invention in the form of a ring-shaped optical component whose purpose is the confinement of the angles under which the reflected light may reach a light-sensitive surface.

Another very effective way of limiting the access of scattered light to the light-sensitive layer is the interposition of an "angular filter" which allows only those rays to get through which fall within a specified limited range. An optical element having such a characteristic is shown in FIG. 5. For the sake of clarity, the sketch contains only the essential details, namely material surface M with an indent E, a light-sensitive layer 32, a diffuser 33, an angular filter body 35, and a number of light rays. The housing, i.e. the tubular part and the different mounts being similar to those illustrated in previous embodiments are not shown.

The angle-limiting device consists of a ring-shaped glass body 35 whose cross-sectional geometry is analogous to that of a Porro prism. The Porro prism is transparent for light rays entering the prism base (hypotenuse) perpendicularly thereto or nearly in the perpendicular direction. Such rays, after a twofold total reflection at the two smaller surfaces $F_1$, $F_2$ emerge from the base with the same angle they had entered with. Rays incident on the base beyond a certain angle of incidence emerge from one of the small surfaces of the prism and are thus eliminated (See $B_1$ and $B_{11}$). The angular range of transmission can be calculated from the following formula.

$$\pm \beta = \pm(45° - \arcsin(1/n)) \quad (3)$$

where n is the refractive index of the glass. For example, if the prism is made of a glass with a refractive index n=1.485, its angular range of transmission becomes $\beta = \pm 2.7°$. If n=1.603, then $\beta = \pm 6.4°$.

This angle-limiting principle has been utilized in the "Porro ring" shown in FIG. 5. The rotationally symmetric glass body 35 has a triangular cross-sectional area, i.e. a right angle at the two outer intersecting conical surfaces and 45° angles at the intersections of the inner conical surface with the outer ones. An annular light-sensitive layer 32, again preferably formed as a surface of revolution about the optical axis, together with a diffuser layer 33 is attached to the upper portion of an inner conical surface $F_3$. A ray $A_{10}$, reflected from the indentation E, reaches the light-sensitive layer 32. However, rays striking the testpiece surface M outside the indent E, like $A_{11}$, generate scattered light rays as $B_1$ and $B_{11}$, for example. The latter, being outside the angular limits given by formula 3, leave the Porro ring through the surfaces $F_1$ and $F_2$ as shown in FIG. 5.

The angle $\psi/2$ between the inner conical surface $F_3$ and the material surface M depends on the cone angle $\psi$ of the indent E, or, if it is a Vickers-indentation (square base pyramid), on the face angle $\psi$. If necessary, the elastic recovery effect, which takes place when the indenter making the indentation being tested is retracted, can be accounted for in the geometry of the ring 35. The indentation angle $\psi$ after removal of the indenter is slightly bigger than $\psi$ under load.

As already mentioned, it is also possible, by applying the disclosed measuring technique, to carry out the indentation area measurement under load. This is the preferred and more accurate technique for a number of reasons, namely 1. To be exact the quantity to be measured is the indentation under load. With respect to metals, the difference between indentation areas while the full test load is applied and after elimination of the load, i.e. after the indenter is removed, is small, amounting to a few percent at most. With respect to plastic materials, however, larger differences may occur.

2. Carrying out the measurement under load takes much less time. The time-consuming manipulations such as taking away the load, removing the indenter from the indent, and placing the area-measuring system over the indentation, are eliminated completely. Instead, the measurement is made as soon as the prescribed loading time has elapsed. Accordingly, rapid hardness testing may be made on large numbers of parts saving time and labor.

3. The contour line of the indent is more discernible when the indenter is in place, i.e. under load, than after its removal. The edges of indents have a finite radius of curvature, as shown in FIG. 4, and these edges are better defined when contact with the indenter is maintained, i.e. under load.

4. Correct hardness measurements for plastics based upon the indentation area become possible.

5. Since no elastic recovery (of the indentation depth) can take place as long as the load is applied, it is possible to draw narrower limits for the admissible angles of the light rays that are allowed to reach the light-sensitive element in the device.

Figure 6:
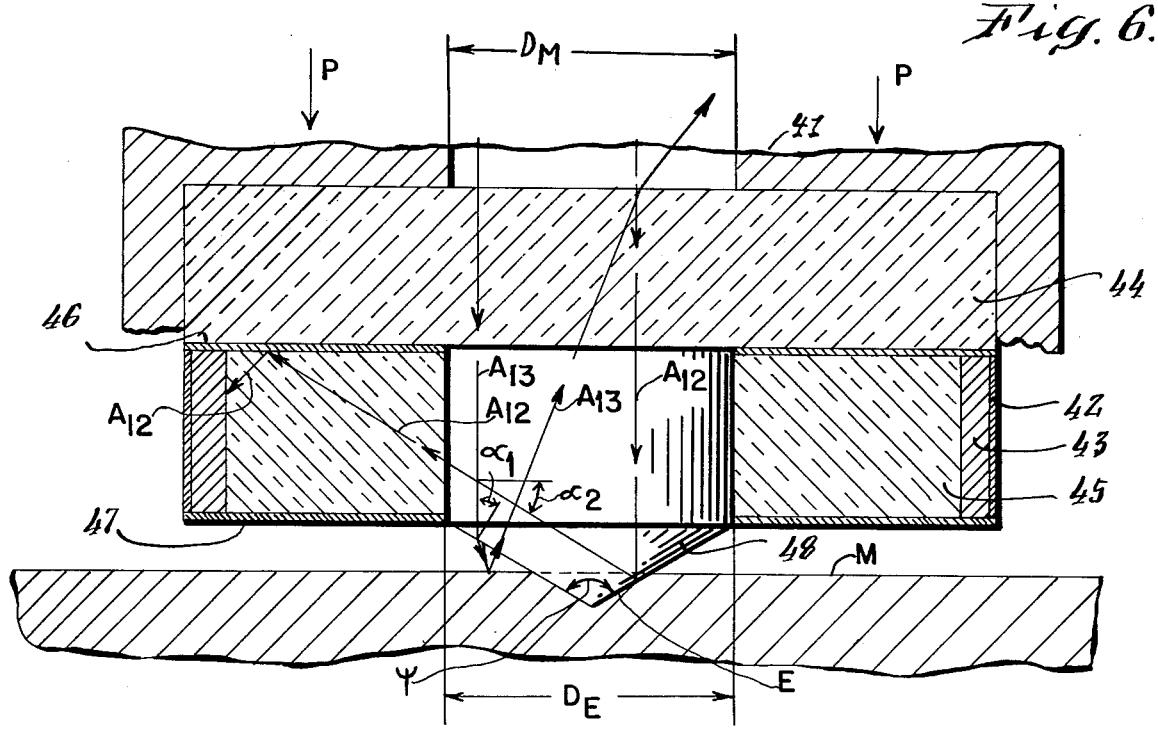
FIG. 6 is another axial sectional view showing parts analogous to FIG. 1 where the measurement in accordance with the present invention is being made while a load is being applied.

FIG. 6 illustrates the measurement of the indentation area under load. As before, merely the lower end of a tubular part 41, through which the scanning light beam is conducted, is shown. A transparent, plane-parallel slab 44, made of a high-strength material like fused alumina, quartz or special glass, is inserted at the lower end of the tubular part 41. Under the lower face of slab 44 is a transparent indenter 48 whose upper face is plane and polished. The indenter 48 is made of a transparent, hard solid like diamond, sapphire or fused alumina. Its diameter $D_E$ corresponds to the maximum diameter $D_M$ of the field of measurement. The lateral surface of the indenter 48 is surrounded by another transparent body 45 the interface being optically cemented to whose outer surface a light-sensitive layer 42, together with a diffuser 43, are attached.

The testing load P is transmitted from part 41 through the slab 44 to the indenter 48. No force has to be transmitted by the transparent body 45. The latter can be made of a transparent plastic or of glass into which the indenter 48 is molded in. The transparent body 45 could be composed of four segments, if necessary, if the indenter's cross-sectional area is square. Further, a readily exchangeable subassembly can be formed from the indenter 48, the surrounding glass body 45, and the light-sensitive layer 42 with the pertinent diffuser 43 by mounting them together in a ring-shaped support. The latter can be provided with threads so that the subassembly can be screwed on to a hardness testing machine.

Total reflection at the interface between the indenter 48 and the surrounding body 45 must not occur for those rays $A_{12}$ which arrive under the nominal angle $\alpha_2 = \psi - 90°$ after reflection from the indent E. The condition for preventing total reflection at that interface is $$\alpha_2 < \alpha_{crit} = \arcsin(n_{45}/n_{48}) \quad (4)$$

where, $n_{45}$ and $n_{48}$ are the refractive indices of the body 45 and the indenter 48, respectively.

Ray $A_{12}$ reaches the light-sensitive layer 42 after reflection at a mirror surface 46 situated between the plane-parallel plate 44 and body 45.

Now, referring to the rays, $A_{13}$, which strike the indenter outside the indentation area, the following condition must be met in order to prevent total reflection at the indenter/air interface:

$$\alpha_1 = \tfrac{1}{2}(180° - \psi) < \alpha_{crit} \quad (5)$$

The Vickers pyramid indenter is made of diamond. Its refractive index is equal to 2.415. Therefore, the critical angle is according to (2): $\alpha_{crit} = 24.46°$. The face angle of the pyramid equals 136°. Hence $\alpha_1 = 22° < \alpha_{crit}$. Thus, the incident light ray is transmitted by the indenter 48, reflected from the material surface M, and then enters the indenter 48 again in such a direction that most of the light energy contained in ray $A_{13}$ is returned to the black center bore of part 41 where it is finally absorbed.

The lower face of the transparent body 45 is coated with an opaque, light-absorbing layer 47. Furthermore, part 41 can be provided with an external, slideable tube, or rubber sleeve (not shown) for preventing the access of contrast-diminishing external light, e.g. daylight to the light-sensitive layer 42.

Special conditions exist when the testpiece is transparent, e.g. clear glass, clear plastics. In such a case, the following must apply $a_1 = \frac{1}{2}(180° - \psi) > a_{crit}$. Then, total reflection will take place at the indenter face bordering on air, while light is transmitted through the indentation area, i.e. where the indenter is making contact with the material surface M. The voltage curve of FIG. 2 will then be reversed. Instead of measuring the time periods $\Delta t$ during which the light intensity is increased, one will measure the periods $\Delta t'$ during which the light intensity is reduced. Accordingly, the indentation area for transparent testpiece follows then from (1): $A = b_y V_x \Sigma(\Delta t')$. This modified measuring procedure is also applicable to dark-colored, opaque substances like graphite and dark, non-transparent plastics.

The totally reflecting indenter, for instance a 120 degree diamond cone, may also be applied to metal hardness testing. This is possible due to the fact that nearly all of the metals reflect the incident light only partially. A steel surface, with a mirror finish, reflects 59 percent of the incident light in the 600 nm range; 45 percent in the 300 nm (ultraviolet) range. If such a totally reflecting indenter is made to penetrate into a steel surface, then a bright peripheral field is observed due to total reflection at the diamond/air boundary along with a relatively darker central field due to specular reflection at the diamond/steel interface. The measuring conditions are particularly favorable since no light is scattered.

Comparable conditions of light reflection, again when using a 120° diamond cone, exist when translucent or opaque plastics are tested. This applies to all colors.

There are cases where it would be advantageous to work with a variant of the embodiment shown in FIG. 6 which contains a diamond indenter with a face angle of 136°. Formula 4 postulates for the refractive index of the surrounding body 45: $n_{45} > 1.744$. A suitable material for the body 45 would be zirconium silicate ($ZrO_2 \cdot SiO_3$) with $n = 1.923$. Even so, due to the still large difference in the refractive indices, the ray $A_{12}$ has a relatively small angle of incidence at the mirror surface 46. Therefore, the light-sensitive layer 42 may be conveniently attached to the lower face of the body 45, instead of being attached to its outer wall. Further, in this latter arrangement the ray $A_{13}$, reflected from the testpiece surface M, would not return to the bore of part 41, but would experience multiple reflection within the indenter 48 before leaving it somewhere underneath the lower face of body 45.

FIGS. 7 and 8 illustrate more complete embodiments for measuring indentation areas, with emphasis on the scanning system. In this embodiment, the light beam, being deflected in two mutually perpendicular directions, is limited in its lateral displacement to the order of magnitude of the indentation diameter. A testing device built for measuring indentation areas of 1 mm², or so, would be fitted with a scanning field area of approximately 4 mm². By providing such a small scanning field, linearity problems are practically eliminated. At the same time, the light beam is displaced laterally in such a way that it remains parallel to itself by means of a mechanical-optical scanning device whereby angular errors that could be caused by scanning systems utilizing rotating mirrors, are avoided.

FIG. 7 and the partial side view of FIG. 8 show a semi-schematic presentation of the essential components of the mechanical-optical device for scanning an indentation area with a raster type scan. The system possesses a light source 52, e.g. a laser, which delivers a narrow, slightly convergent light beam A. The shaft of an electric motor 53 is on one side linked directly to a glass plate 54 and on the other side, via reduction gears 55, 56 and 57, to a second glass plate 58. The two glass plates 54, 58, whose rotational axes are perpendicular to each other, are thus made to rotate by the same motor, so that their speed ratio $n_2/n_1$ is constant. Owing to the reduction gears 55, 56 and 57, the rotational speed of the second glass plate, 58, is very much lower than that of the first plate 54. The parts described so far are fastened to a rigid frame 59 which holds a stop 51 whose aperture F determines the extent of the scanning field of the device which should conform with the linear range of the beam deflectors.

The light beam A travels from the light source 52 through the two glass plates 54 and 58, and through the aperture F of the stop 51 to the material surface M containing the indent E. Between the stop 51 and the material surface M lies a tubular part such as part 1, 11, 21 or 41, which for ease of illustration and clarity have not been shown, where the light-sensitive layer and the optical elements for the detection of the reflected rays are accommodated.

The deflection of a light ray caused by a rotating plane-parallel glass plate is as follows:

$$a = t_p \left[ 1 - \frac{\frac{1}{n_p} \cdot \cos\phi}{\sqrt{1 - \left(\frac{1}{n_p}\sin\phi\right)^2}} \right] \sin\phi \quad (6)$$

where $n_p$ is the refractive index of the plate, $\phi$ the angle of rotation equalling the angle of incidence, and $t_p$ the plate thickness. From this formula, the deflection velocity at the moment when $a = 0$ ($\phi = 0$) is:

$$V_{x(y)} = \left(1 - \frac{1}{n_{p1(2)}}\right) \cdot 2\pi n_{1(2)} t_{p1(2)} \quad (7)$$

where $n_1$ = rotational speed (rps), $n_{p1}$ = refractive index, and $t_{p1}$ = thickness of the first glass plate, i.e. the one which deflects the beam in the X-direction, and (2) refers to the second glass plate which produces the Y-scan. The thicker the glass plate and the bigger its refractive index, the better the linearity requirement is met for a given deflection $a_F$ which is determined by the magnitude of the field F in FIG. 7.

The two glass plates 54 and 58 provide, within the limits set by the extension of the scanning field F, the linear deflections $a_x(t)$ and $a_y(t)$. Owing to the constant rotational speeds $n_1 >> n_2$ one obtains also constant deflection velocities $v_x >> v_y$. When the two glass plates 54 and 58 are spinning, then the light spot generated on the material surface M by the light beam A crosses the scanning field F, containing the indentation E, in two directions. As a result, the light-sensitive surface or detector built into the device produces the already outlined voltage curves E(t) (See FIG. 2).

FIG. 9 illustrates one convenient type of electronic system which may be used for the evaluation of the E(t) curves. According to this arrangement, the voltage E generated by photocell 62 by reflections from the indentation under test controls a gate circuit 61 which is linked to a counting circuit 68. The voltage E(t) produced by the light-sensitive element 62 after amplification by amplifier 63 is fed into a trigger circuit 64 having means for setting a threshold voltage $E_s$. As long as $E(t) > E_s$, the gate 61 permits the passage of the pulses coming from a pulse generator 67 with a pulse frequency $f_z$. The number of pulses passing through the gate 61 becomes then $N = f_z t_d$ where $t_d = \Sigma(\Delta t)$ is the time the gate is open during one complete scan of the measuring field. Thus, N becomes proportional to the indentation area A.

The pulse frequency $f_z$ is generated, according to FIG. 9, in the following manner. The electric motor 53 (See FIGS. 7 and 8) drives a generator 65 with a rotational speed $n_1$ so that a signal with a primary frequency $f_g = \mu_1 n_1$ is produced. This serves as input for a frequency multiplier 66 having a multiplying factor $\mu_2$. Finally, the signal of the frequency $\mu_2 f_g$ is passed through a pulse-shaping network 67. The output consists now of a series of short pulses with a pulse frequency $f_z = \mu_2 g = \mu_1 \mu_2 n_1 = m n_1$. The pulses permitted to pass through the gate 61 are fed into the counting circuit 68. If N is equal to the number of counted pulses, the corresponding area becomes $A = kN$. It is recommended that the system be constructed such that the factor k is equal to a power of ten. By connecting a small computer circuit 70 to the counter 68 the desired hardness values are calculated and displayed or printed out by a display 69.

Equations (1) for the area A and (7) for the deflection velocities $v_x$, $v_y$ in conjunction with the line width formula $b_y = v_y/(p_1 n_1)$, where $p_1$ is the number of plane transparent flat faces of the rotating glass body 54 used for the beam deflection in the X-direction, provide a specific expression for the indentation area A, written below. In the example given in FIGS. 7 and 8, $p_1 = 2$. If a hexagonal prism is used instead of the plane-parallel glass plate, then $p_1 = 6$. The number $p_1$ also indicates how many X-scans are taking place per revolution of the glass body 54. Now, with $t_d = N/f_z$ and $f_z = m n_1$ and assuming that $v_x = $const, $v_y = $const, and $n_1 > > n_2$, one obtains for the indentation area $$A = \frac{v_x b_y}{m n_1} N \qquad (8)$$

$$= \frac{4\pi^2 n_2}{p_1 m n_1} (1 - \frac{1}{n_{p1}})(1 - \frac{1}{n_{p2}}) t_{p1} t_{p2} N = kN$$

It should be noted that the plate thickness $t_{p1}$, $t_{p2}$ are invariable and exactly measurable; that the refractive indices $n_{p1}$, $n_{p2}$ of the optical glasses employed are known and cannot change; that the rotation speed ratio $n_2/n_1$ is fixed if, for example, gears are used; that the face number $p_1$ is a fixed quantity; and, finally, that the frequency multiplier m is invariable too. Therefore, the indentation area is $A = kN$, where k is a calculable, immutable factor.

The electronic system, in FIG. 9, has been supplemented by an oscilloscope 71 which shows the geometry (shape) of the indentation.

There is still one variable left in the system disclosed in FIG. 9 and that is the trigger threshold voltage $E_s$. If $E_r$ is the residual voltage caused by light being scattered from the testpiece surface beyond the indent, then the median voltage will be equal to $\frac{1}{2} \cdot (E_r + E_{max})$ (See FIG. 2). As known in the art, $E_s$ may be adjusted automatically by electronic means so that at all times $E_s \approx \frac{1}{2}(E_r + E_{max})$. This is called "electronic interpolation". In this manner the uncertainty, caused by the finite gradient of the E(t) curve's flanks, is largely eliminated. It can be seen in FIG. 2 that the flank angle is smaller than 90° as a consequence of the finite light spot diameter and the finite curvature of the indentation edges.

A simple embodiment is shown in FIG. 10 for the measurement of an indentation diameter under load. The test load P is effective on the cylindrical part 80 whose tubular continuation 81 is terminated by a plate carrying an indenter 88 which is resting on the material surface M. The light source (laser) 82 is mounted inside section 81 and can be displaced in the X-direction by means of a micrometer screw 84. The light beam A reaches the material surface M through the indenter 88. The light beam is centered relative to the indenter 88 in such a way that it passes through the point (apex) of the latter when the light source 82 is moved in the X-direction from one side to the other.

The light that is reflected from the indentation reaches the light-sensitive layer (not shown) in the same manner as outlined in the description of FIG. 6. The resulting voltage E(x) is amplified by amplifier 83 and fed into a voltmeter 85. In addition to or instead of the voltmeter 85, an XY-recorder may be employed. The shape of the E(x) curve is identical with the one shown on the left side (a) of the diagram in FIG. 2.

Of course, the light source 82 may be moved orthogonally to the X-direction, i.e. from the Y-direction from one side to the other also through the apex of the indenter 88, and the area of the indent may be calculated using the two orthogonal diameters of the indent. The scanning of the orthogonal axis diameters of the indent may be accomplished by manually scanning in one direction and then the other direction or the scanning may be automatically controlled in sequence.

The type of micrometer utilized for making this measurement is a matter of choice. The equipment, in its simplest form, would be fitted with a standard screw micrometer. More expensive equipment could be fitted with a motor-driven micrometer combined with a digital readout system.

Since other changes and modifications varied to fit particular operating requirements and environments will be apparent to those skilled in the art, the invention is not considered limited to the examples chosen for purposes of illustration, and covers all changes and modifications which do not constitute a departure from the true spirit and scope of this invention.

What is claimed is:

1. The method of measuring the magnitude of hardness testing indentations in solid surfaces utilizing a beam from a light source which at the point of incidence is small with respect to the size of the indentation being measured and which is directed at substantially normal incidence to the indented surface comprising the steps of:
   (a) applying a loading force through a transparent indenter in the same direction as the incident light beam,
   (b) scanning an indentation made in the solid surface under test through said indenter in at least one direction by moving said light beam across the working surface of the indenter at substantially normal incidence to the plane of said solid surface,
   (c) encircling the light exit surface of the transparent indenter with a light-sensitive surface in accordance with the geometries of said indentation and indenter which does not interfere with the scanning of said indentation, said light sensitive surface receiving light specularly reflected from said indentation;

(d) measuring the intensity of the specularly reflected light from said indenter and indentation within a predetermined angular range covered by said light-sensitive surface, and (e) determining the magnitude of said indentation utilizing the intensity variation of the specularly reflected light from said indenter and indentation occurring when the light beam arrives at or exits the indentation.

2. Apparatus for measuring the magnitude of hardness testing indentations in solid surfaces utilizing a beam from a light source which is small with respect to the size of the indentation being measured comprising:

(a) a transparent indenter which is transparent to the light beam, (b) means for applying a load to said surface through said transparent indenter while the measurement is being made, said light beam being directed through said transparent indenter, (c) scanning means for scanning and displacing said light beam across an indentation relative to the fixed surface being tested, the light beam displacement being perpendicular to the direction of the light beam propagation, (d) detection means for detecting the light intensity of the light beam specularly reflected from said indentation within a predetermined angular range surrounding the indentation which differs from the direction of incidence of said light beam whereby the detected light is primarily specularly reflected from the indentation, (e) said detection means being a light-sensitive surface encircling said indentation, and (f) measuring means coupled to said detection means for determining the magnitude of said indentation.

3. The apparatus set forth in claim 2 having a tubular means which is positioned on the surface being tested and having a diameter larger than the diameter of the indentation being measured and through which said light beam is projected, said tubular means containing said light sensitive surface and having said transparent indenter mounted on a lower portion thereof in contact with said surface being tested.

4. The apparatus set forth in claim 3 having a transparent transmission body in contact with said transparent indenter through which said light beam passes and through which a test load may be applied to said indenter.

5. The apparatus set forth in claim 4 wherein said light sensitive surface is attached to an external surface of a transparent body surrounding said indenter, and a reflective surface is positioned between said transmission body and said transparent body.

* * * * *